US005895394A

United States Patent [19]
Kienzle et al.

[11] Patent Number: 5,895,394
[45] Date of Patent: Apr. 20, 1999

[54] SURGICAL APPLICATOR FOR U-SHAPED CLIPS

[75] Inventors: Karl-Ernst Kienzle, Immendingen; Rupert Mayenberger, Rielasingen; Markus Nesper, Tuttlingen; Dieter Weisshaupt, Immendingen, all of Germany

[73] Assignee: Aesculap Ag & Co. Kg, Tuttlingen, Germany

[21] Appl. No.: 08/819,305

[22] Filed: Mar. 18, 1997

[30] Foreign Application Priority Data

Sep. 24, 1996 [DE] Germany ............. 296 16 632 U

[51] Int. Cl.[6] ........................................ A61B 17/04
[52] U.S. Cl. ........................... 606/143; 606/142
[58] Field of Search ........................... 606/142, 143

[56] References Cited

U.S. PATENT DOCUMENTS

| 4,527,726 | 7/1985 | Assell et al. ............... 227/19 |
| 4,646,740 | 3/1987 | Peters et al. ............... 606/143 |
| 5,112,343 | 5/1992 | Thornton ................... 606/143 |
| 5,282,807 | 2/1994 | Knoepfler .................. 606/143 |
| 5,422,835 | 6/1995 | Green et al. .............. 606/143 |
| 5,527,318 | 6/1996 | McGarry ................... 606/143 |
| 5,542,949 | 8/1996 | Yoon ....................... 606/143 |
| 5,607,436 | 3/1997 | Pratt et al. ................ 606/143 |
| 5,626,586 | 5/1997 | Pistl et al. ................ 606/143 |

FOREIGN PATENT DOCUMENTS

| 0 406 724 | 1/1991 | European Pat. Off. . |
| 0 409 569 | 1/1991 | European Pat. Off. ........... 227/19 |
| 43 03 544 | 9/1993 | Germany . |

*Primary Examiner*—Gary Jackson
*Attorney, Agent, or Firm*—Barry R. Lipsitz; Ralph F. Hoppin

[57] ABSTRACT

In a surgical applicator for U-shaped clips comprising a handle, a tubular shaft adjoining the handle, a forceps-type applicator tool at the free end of the tubular shaft, a closing mechanism for the applicator tool arranged in the tubular shaft and actuatable from the handle, an advancing mechanism for the clips arranged in the tubular shaft and also actuatable from the handle, two separate actuating elements on the handle, each being movable between a rest position and a work position, one of the actuating elements being associated with the closing mechanism and the other with the advancing mechanism, in order to improve the safety measures and the actuating aids, it is proposed that a locking member be mounted on one of the actuating elements and enter into operative connection with the other actuating element, thereby to prevent each of the two actuating elements from moving so long as the respective other actuating element is not in its rest position.

37 Claims, 5 Drawing Sheets

SURGICAL APPLICATOR FOR U-SHAPED CLIPS

BACKGROUND OF THE INVENTION

The invention relates to a surgical applicator for U-shaped clips comprising a handle, a tubular shaft adjoining the handle, a forceps-type applicator-tool at the free end of the tubular shaft, a closing mechanism for the applicator tool arranged in the tubular shaft and actuatable from the handle, an advancing mechanism for the clips arranged in the tubular shaft and also actuatable from the handle, two separate actuating elements on the handle, each being movable between a rest position and a work position, one of the actuating elements being associated with the closing mechanism and the other with the advancing mechanism.

Such a surgical applicator is known from DE 44 29 084 C1.

When applying the clips from such an applicator, it is important for the operator to be guided by the instrument itself in the sequence of the movements, and for it to be thus ensured that the instrument will only permit actions which are correct. It should be ensured that a clip is first advanced from the magazine into the applicator tool and that this operation is, in any case, completed before it is possible to actuate the closing mechanism.

It is also purposeful to exclude another advance of a clip in the direction towards the applicator tool so long as the closing mechanism has not terminated its closing operation, and, therefore, so long as it is not yet in the open position again. Finally, two clips must, at any rate, be prevented from being unintentionally advanced one immediately after the other into the applicator tool.

SUMMARY OF THE INVENTION

The object underlying the invention is to so design a surgical applicator of the generic kind that these safety measures and actuating aids are guaranteed.

This object is accomplished in accordance with the invention in a surgical applicator of the kind described at the outset in that a locking member is mounted on one of the actuating elements and enters into operative connection with the other actuating element, thereby preventing each of the two actuating elements from moving so long as the respective other actuating element is not in its rest position.

In other words, each of the two actuating elements is only movable when the respective other actuating element is in its rest position. Simultaneous actuation is excluded. It is also ensured that one operation is completed, for example, the advance of a clip into the applicator tool, before a further operation can be started.

In accordance with a preferred embodiment, provision is made for the locking member on the one actuating element to be movable between two positions, namely a first release position in which the one actuating element is freely movable when the other actuating element is in its rest position, and a lock position in which the one actuating element, in any position of the other actuating element, is locked in its movement by the locking member contacting the other actuating element.

Such a locking member enables actuation of an actuating element to also be made impossible when the other actuating element is in the rest position. For example, this could be carried out manually by switching the locking member from the release position to the lock position.

Herein it is particularly advantageous for the locking member to be movable from the release position to the lock position by the movement of the one actuating element from the rest position to the work position and, at the end of this movement, by contact with the other actuating element. Accordingly, at the end of the movement of an actuating element, the locking member is automatically moved to the lock position, and it is thereby ensured that this actuating element can still be moved back to its rest position but not to its work position again. Double actuation of an actuating element is thus excluded.

It is particularly advantageous for a spring detent means to releasably fix the locking member in both the release position and the lock position.

In accordance with a preferred embodiment, provision is additionally made for a reversible freewheel mechanism to be associated with the one actuating element so as to allow movement of the actuating element in one direction only, with the direction of movement thereof only being reversible when the actuating element has reached the end points of its path of movement. Such a freewheel mechanism ensures that upon movement of an actuating element from the rest position to the work position, this movement is carried out to the end of the path of movement. Return movement after partial movement is not possible. This ensures that each movement of an actuating element is carried out completely before return movement to the rest position is possible. Such freewheel mechanisms are known, for example, from DE 44 29 084 C1. Reference is made expressly to the structural design of such a freewheel mechanism described therein.

In a preferred embodiment, provision is made for the locking member to carry a projection adapted to be pressed in resiliently and having on one side thereof a flat slide flank and on the other side thereof a steep retaining flank for a part of the other actuating element sliding along the projection, for the projection to only interact with the sliding part when the locking member is in the lock position, and for the projection to be arranged such that the sliding part of the other actuating element contacts the steep retaining flank when the first actuating element is in its rest position.

This embodiment ensures that after its complete movement to the work position, the first actuating element can be moved back to the rest position again, however, after attaining the rest position is no longer movable, but is locked. Double actuation is thus excluded.

It is expedient for the locking member to be movable from the lock position to the release position by the movement of the other actuating element from the rest position to the work position and, at the end of this movement, by contact with the other actuating element. Thus, switching of the locking member back to the release position is also effected by actuating the actuating elements, more particularly, by actuating the other actuating element as far as its work position.

Although this could, in principle, be chosen differently, provision is made in accordance with a preferred embodiment, for the one actuating element to be associated with the advancing mechanism and the other actuating element with the closing mechanism.

A structural embodiment wherein the actuating elements are designed as swivel levers on the handle for rotation about an axis extending transversely to the longitudinal axis of the tubular shaft, as is known per se from DE 44 29 084 C1, is particularly expedient.

In a preferred embodiment, the locking member is a disc mounted on the first actuating element for rotation about an axis extending parallel to the axis of rotation of the first actuating element between the release position and the lock position.

This disc may have two edge recesses lying alongside each other, in which a detent member displaceable on the first actuating element in the direction towards the axis of rotation of the disc and resiliently pressed against the edge of the disc engages. The disc is fixed by this detention in the release position and in the lock position, but can be swivelled to the respective other position on overcoming a certain torque.

It is expedient for the disc to be arranged in a recess of the one actuating element which is arranged on the part of the one actuating element located opposite the handle part of the one actuating element and which is open at the side towards the other actuating element.

This recess can be partially closed by a cover plate.

In a preferred embodiment, provision is made for the disc to have an angular projection adapted to be pressed in resiliently with an edge with two edge sections, for a projection of the other actuating element to be arranged beside this edge, and for this projection to run along one edge section when the one actuating element is moved from its rest position to its work position, with the other actuating element in its rest position, and along the other edge section when the other actuating element is moved from the rest position to the work position, with the one actuating element in its rest position. Accordingly, the contour of the edge is adapted to the directions of movement of the projection on the other actuating element, with this direction of movement resulting, on the one hand, from the movement of the one actuating element, with the other actuating element at rest, and, on the other hand, from pivotal movement of the other actuating element, with the one actuating element at rest. It is advantageous for the edge sections to be of arcuate shape.

In particular, provision may be made for the edge sections to meet essentially at a right angle and for the path of movement of the projection on the other actuating element, upon swivel movement thereof, to extend essentially perpendicular to the one edge section and parallel to the other edge section. This special configuration makes it possible for the projection on the other actuating element, upon movement of the one actuating element from the work position to the rest position, to slide on the projection and press it resiliently into the disc, with the projection on the other actuating element releasing the projection on the disc once the one actuating element has reached the rest position. Renewed movement of the one actuating element is then excluded because during this renewed movement the projection on the other actuating element strikes the projection, more specifically, not in the direction in which it is pressed in resiliently, but perpendicularly thereto. This prevents double actuation of the one actuating element.

In accordance with a preferred embodiment, it is particularly expedient for the projection to be mounted on the one actuating element for rotation about the same axis of rotation as the disc and to be rotated relative to the disc by a swivel spring into a position protruding over the disc.

This swivel spring can, for example, be a spring rod or a leaf spring.

It is also expedient for the projection to be in the form of a lamina and to be received in a central recess of the disc.

Further provision is made for the disc to have stop faces with which the projection of the other actuating element comes into contact and swivels the disc from the release position to the lock position and vice versa when the one or the other actuating element is in the work position. Therefore, by actuation of the actuating elements from the rest position to the work position, a switching over of the disc occurs automatically. This disc is swivelled from the release position to the lock position when the one actuating element is completely swivelled to the work position. When, on the other hand, the other actuating element is completely swivelled to the work position, it switches the disc from the lock position to the release position again.

Provision may be made for the projection on the other actuating element to be a sidewardly protruding pin.

The following description of preferred embodiments of the invention serves in conjunction with the drawings to explain the invention in greater detail.

DETAILED DESCRIPTION OF THE INVENTION

The clip applicator illustrated in the drawings comprises a handle 1 and a tubular shaft 2 rotatable about its longitudinal axis and releasably held on the handle 1. The outer diameter of the tubular shaft 2 is slight in comparison with its length. For example, the length can be 25 cm, the outer diameter 10 mm.

Two jaws 4 of a forceps-type applicator tool are mounted at the free end of the tubular shaft 2 for swivel movement about a common swivel axis 3. These can be opened and closed from the handle 1 via a closing mechanism arranged in the interior of the tubular shaft. For this purpose, the handle 1 is rigidly connected to a first handle part 5, relative to which a second handle part 6 is mounted for swivel movement on the handle 1. This second handle part 6 is articulatedly connected to a push-and-pull rod in the form of a sleeve 7 which extends through the entire tubular shaft 2 as far as the closing mechanism 8. By swivelling the handle parts 5 and 6 relative to each other, the jaws 4 of the applicator tool can thus be opened and closed.

In the interior of the tubular shaft 2, a number of clips 10 are arranged one behind the other in a magazine 9. The clips 10 can be pushed forwards out of the magazine 9 in between the jaws 4 of the applicator tool by an advancing mechanism 11. These details are not illustrated individually in the Figure, and reference is to be had in this connection to, for example, DE 44 29 084 C1 in which such a construction is described in detail.

The advancing mechanism 11 comprises a push-and-pull rod 12 which extends in the interior of the sleeve 7 as far as the handle 1 and is rotatably connected there to a swivel lever 13 mounted on the handle 1. When the swivel lever 13 is actuated, i.e., swivelled in the direction towards the stationary handle part 5, the push-and-pull rod 12 is pushed forwards and thereby moves a clip 10 out of the magazine 9 in between the jaws 4.

As described in DE 44 29 084 C1, a freewheel mechanism can be associated with the push-and-pull rod 12 to ensure that the push-and-pull rod can only be moved in one direction, with this direction of movement automatically reversing once the push-and-pull rod has reached the end point of its path of movement. This is not illustrated in the drawings and is not described in detail herein.

The swivel lever 13 for actuating the advancing mechanism 11 forms one actuating element, the handle part 6 adapted for swivel movement for actuating the closing mechanism 8 forms another actuating element. The two actuating elements fulfill different functions and are correlated in the manner described hereinbelow such that either the one or the other function only can be carried out and such that it is ensured that these functions are employed correctly, and that it is, therefore, not possible for two clips to be advanced without one clip having meanwhile been properly applied by actuation of the closing mechanism 8.

Figures 1, 2:
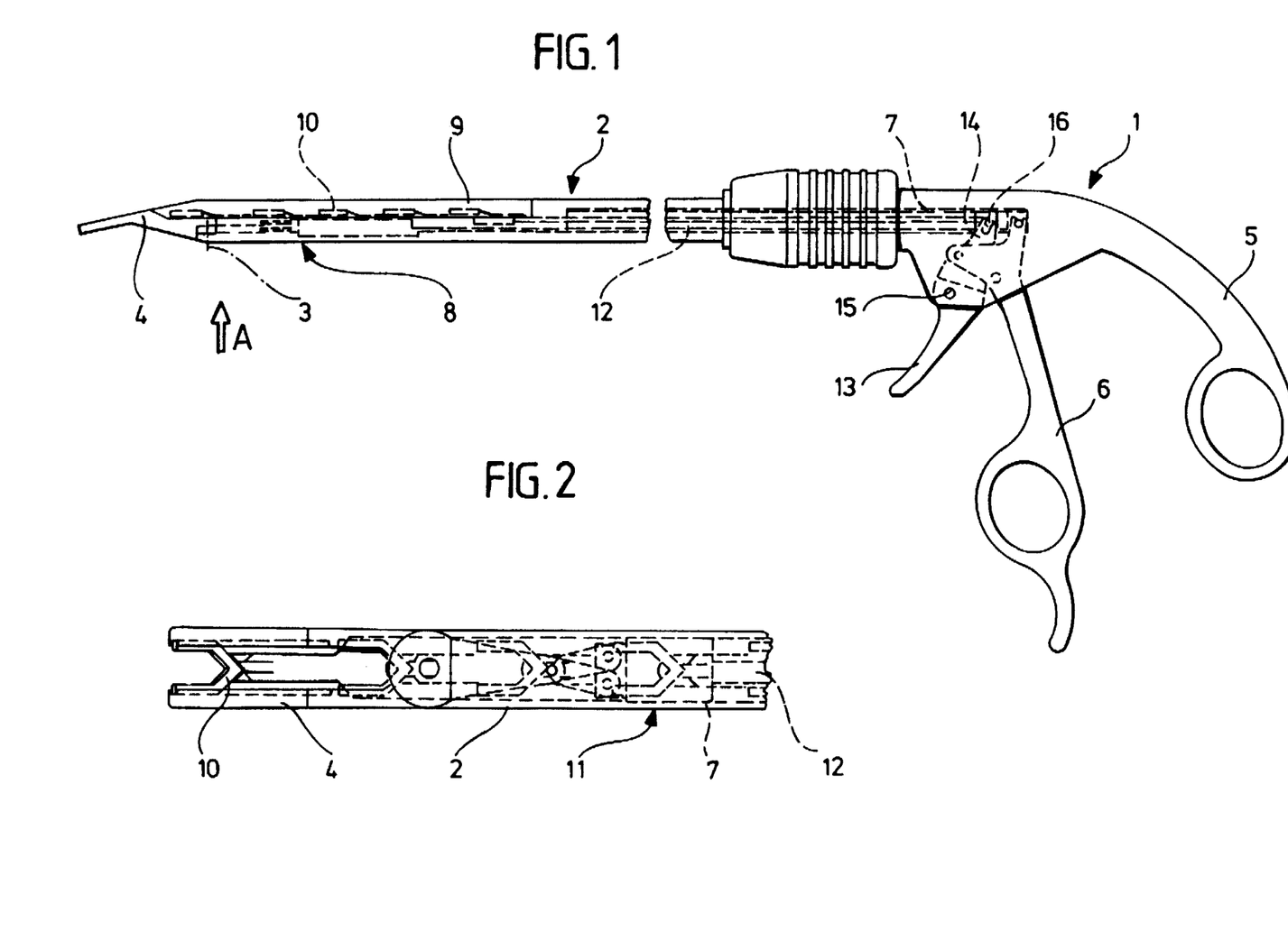
FIG. 1 a schematic side view of a clip applicator with two actuating elements adapted for swivel movement.
FIG. 2 an enlarged view of the tool area of the applicator of FIG. 1 in the direction of arrow A.
Figure 3:
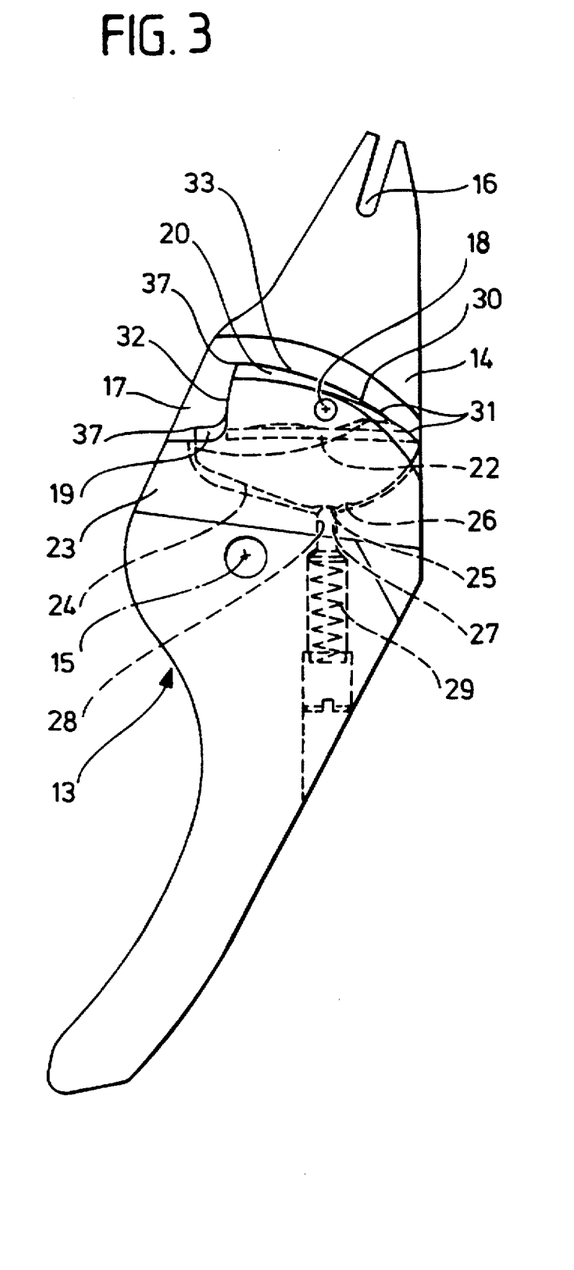
FIG. 3 a side view of the one actuating element.
Figure 4:
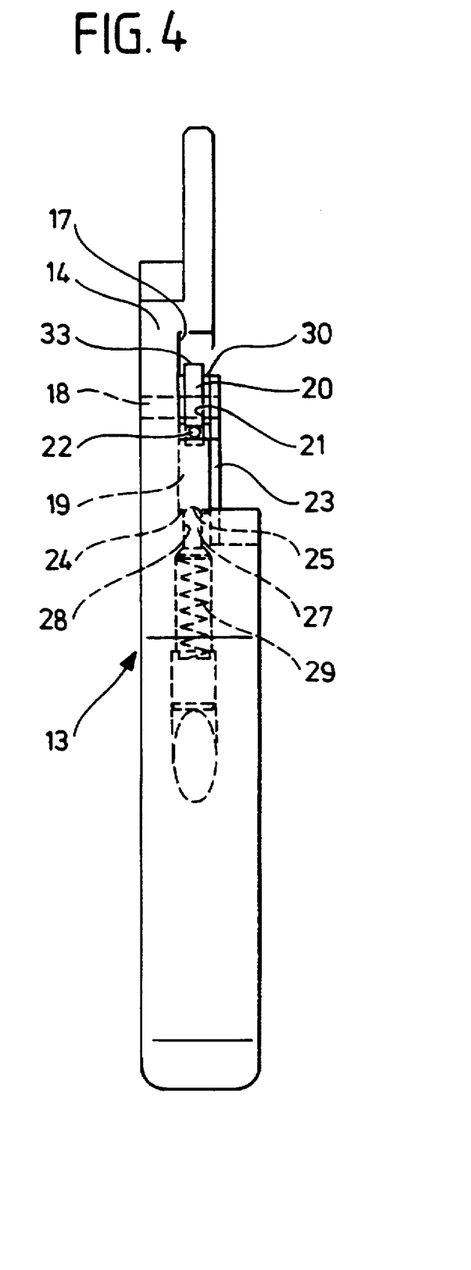
FIG. 4 a front view of the one actuating element according to FIG. 3.

For this purpose, the swivel lever 13 comprises in its section 14 between its axis of rotation 15 extending transversely to the longitudinal axis of the tubular shaft 2 and a swivel-slide-joint connection 16 with the push-and-pull rod 12 a chamber 17 which is open at the side and into which a bearing pin 18 extending parallel to the axis of rotation 15 projects. A disc 19 and a lamina 20 are rotatably mounted on this bearing pin 18. The lamina 20 extends into a central pocket 21 of the disc 19 and so its rotational movement relative to the disc 19 is delimited in both directions. A bending spring 22 fixed in the disc 19 projects into the pocket 21 and rests against the underside of the lamina 20 in such a way that the lamina 20 is swivelled into a stop position, in the illustration in FIG. 3 in the clockwise direction. The lamina 20 can be rotated anticlockwise against the deformation of the bending spring 22.

The chamber 17 is partially closed on its open side by a cover plate 23 which serves as abutment for the bearing pin 18.

The disc 19 can only be swivelled through a limited angle in the chamber 17. A detent member 27 projects into two recesses 25 and 26 arranged alongside each other at the lower edge 24 of the disc 19. The detent member 27 is mounted for displacement in a bore 28 of the swivel lever 13. This bore extends radially in the direction towards the axis of rotation formed by the bearing pin 18. The detent member 27 is acted upon by a pressure spring 29 and thus resiliently engages the recesses 25 or 26. In this way, the disc can be fixed in two different positions which, however, are both releasable, i.e., by applying a certain torque the disc can be swivelled from one end position to the other end position.

The upper edge 30 of the disc extends over a first section 31 approximately concentrically with the axis of rotation 15 of the swivel lever 13, in an adjoining second section 32 essentially perpendicular thereto, i.e., approximately radially in relation to the axis of rotation 15. The two sections 31 and 32 extend towards each other at a right angle.

The upper edge 33 of the lamina 20 is of essentially the same design, but this upper edge 33 projects in the area in which the two sections meet each other at a right angle, under the action of the bending spring 22, slightly over the upper edge 30 of the disc 19. By swivelling the lamina 20 against the action of the bending spring 22, this projecting upper edge 33 can be lowered so far that it coincides essentially with the upper edge 30 of the disc 19.

The section 32 of the upper edge 30 of the disc 19 extending essentially radially in relation to the axis of rotation 15 continues at its end facing the axis of rotation 15 into a projection 34 protruding essentially perpendicularly from the section 32. Like the section 31 of the upper edge 30 at the opposite end of the disc 19, the projection 34 forms a stop surface for a pin 35 which is arranged on the handle part 6 on an arm 36 projecting transversely from the handle part 6 and which projects immediately beside the upper edge 30 of the disc 19 into the chamber 17 of the swivel lever 13.

The way in which these parts cooperate upon movement of the swivel lever 13 and the handle part 6 will be described hereinbelow with reference to FIGS. 5 to 8.

Figure 5:
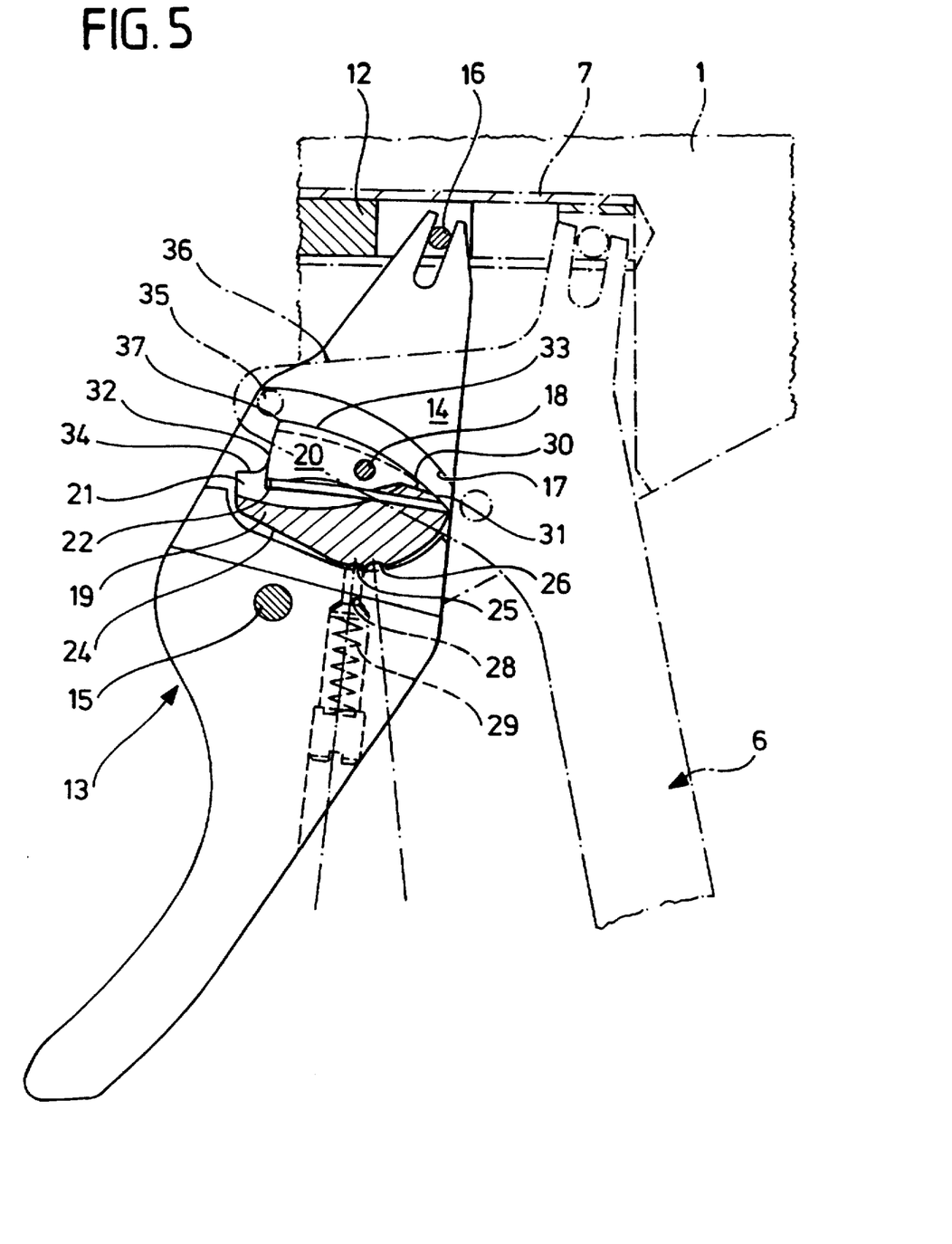
FIG. 5 a side view of the two actuating elements (in continuous and dot-and-dash lines, respectively) with both actuating elements in the rest position and the disc in the release position.

Initially, the swivel lever 13 and the handle part 6 are in their rest position in which the sleeve 7 and the push-and-pull rod 12 are drawn back in the tubular shaft (FIG. 5).

The disc 19 is in its release position in which the upper edge 30 is lowered in the area in which the sections 31 and 32 meet, i.e., in FIG. 5 in the anticlockwise swivelled position. The pin 35 of the handle part 6 is arranged above the projection 37 which is formed by the sections meeting at a right angle at the upper edge 33 of the lamina 20.

Starting from this position, the swivel lever 13 can be swivelled in the direction of arrow B (FIG. 6) so the push-and-pull rod 12 is pushed forward in the tubular shaft 2 and the advancing mechanism 11 for the clips 10 is actuated. During this swivel movement, the pin 35 is spaced from the section 31 of the upper edge 30 of the disc 19 and from the corresponding upper edge of the lamina 20 until the pin 35 contacts the end of the section 31 of the upper edge 30 at the end of the swivel movement and during the further swivel movement of the swivel lever 13 thereby swivels the disc 19, in turn, about the axis of rotation of the bearing pin 18 so the detent member 27 projects into the recess 26. The disc 19 is then in the so-called lock position in which the projection 37 is raised in relation to the release position.

Figure 6:
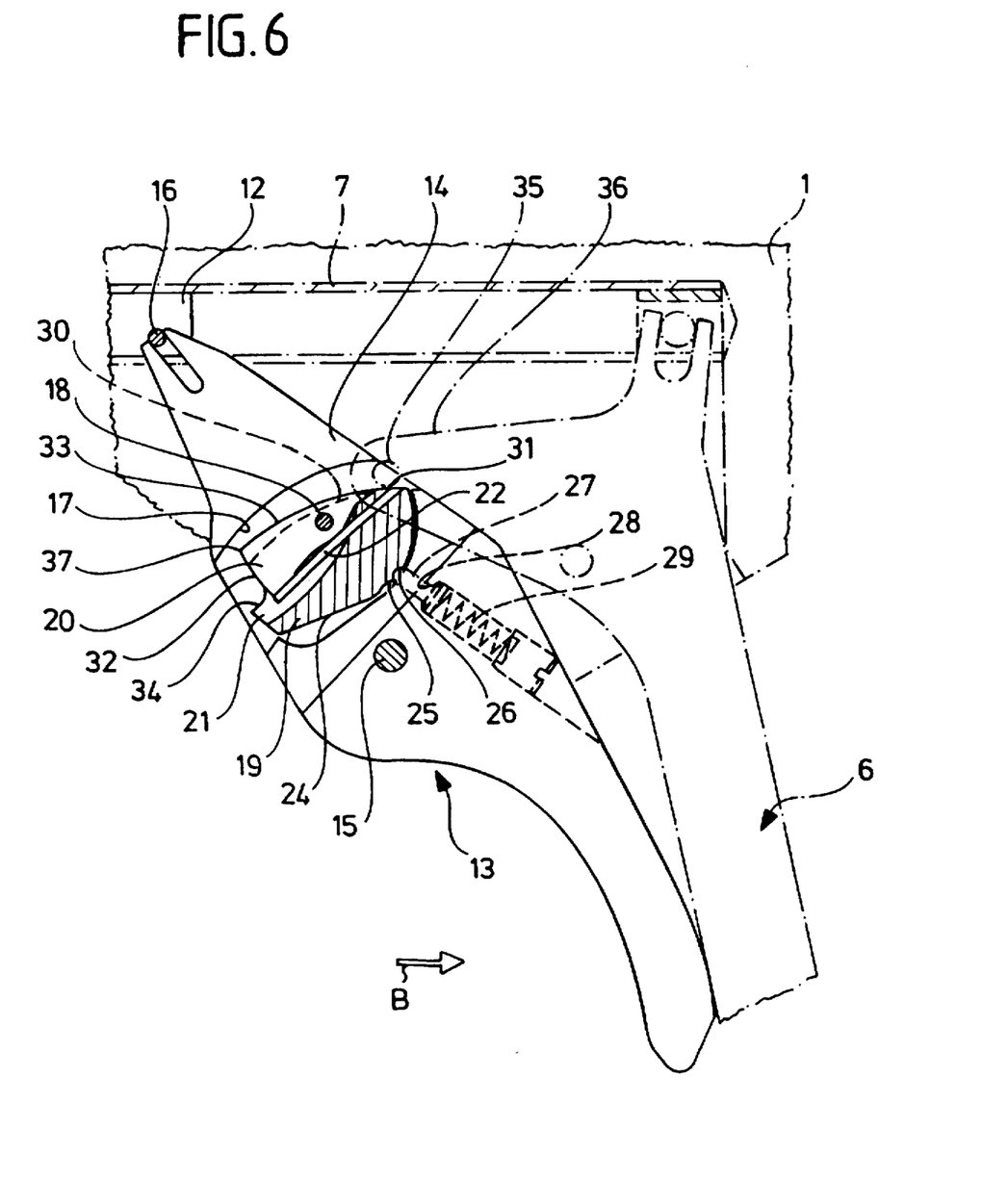
FIG. 6 a view similar to FIG. 5 with the one actuating element in the work position and the other actuating element in the rest position.

During the entire swivel movement of the swivel lever 13, the handle part 6 is prevented from swivelling from the rest position as the pin 35 contacts the section 31 of the upper edge 30 of the disc 19 during such swivel movement.

On the other hand, it is readily possible to swivel the swivel lever 13 back again, but if the described freewheel mechanism is used, then only if the swivel movement of the swivel lever 13 has been completed, i.e., if the swivel lever 13 has been swivelled completely from the rest position to the work position.

The freewheel mechanism is thereby reversed in its direction of movement and only then enables the swivel lever 13 to be swivelled back from the work position to the rest position.

Figures 7, 8:
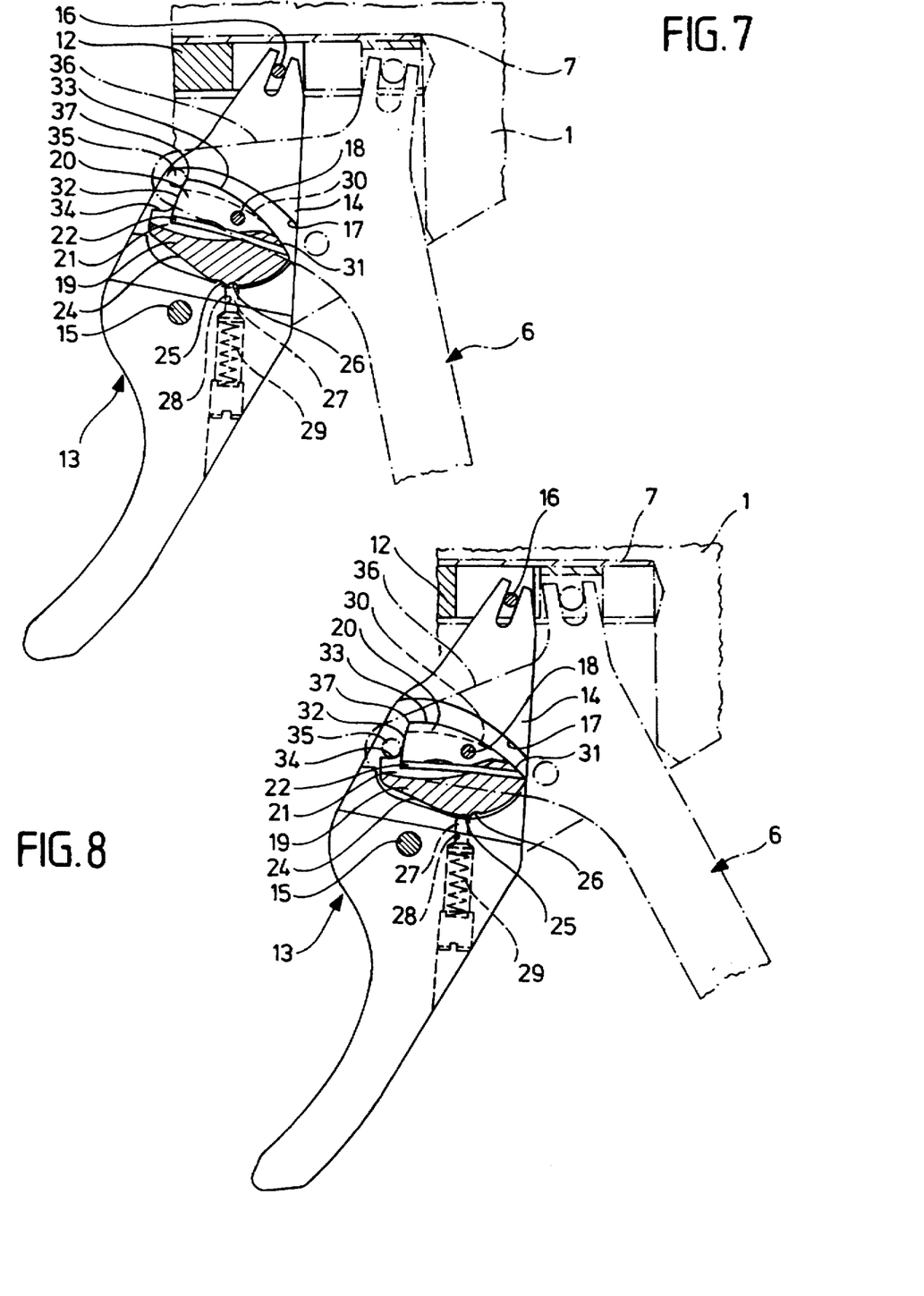
FIG. 7 a view similar to FIG. 5 with both actuating elements in the rest position and the disc in the lock position.
FIG. 8 a view similar to FIG. 5 with the one actuating element in the rest position and the other actuating element in the work position.

During this return swivel movement of the swivel lever 13 to the rest position, the pin 35 of the handle part 6 slides along the upper edge of the lamina 20 and finally swivels this lamina 20 against the action of the bending spring 22 and so the pin 35 can slide past the projection 37 formed by the lamina 20, although this projection 37 is arranged higher owing to rotation of the disc 19 into the lock position, and, with the bending spring 22 in the undeformed state, projects into the path of movement of the pin 35 (FIG. 7). After passing the projection 37, however, the latter springs out again under the action of the bending spring 22 so the pin 35 in the area of the projection 37 contacts the edge extending essentially radially to the axis of rotation 15, and this prevents the swivel lever 13 from being able to swivel out of the rest position into the work position again.

On the other hand, it is now readily possible to swivel the handle part 6 from the rest position to the work position, by means of which the sleeve 7 is pushed forwards and the closing mechanism 8 is actuated. The pin 35 then slides along the section 32 of the upper edge 30 of the disc 19 until it contacts the projection 34 and during the last part of the movement of the handle part 6 thereby takes the disc 19 along with it and swivels it into the release position again, i.e., the detent member 27 now projects into the recess 25 (FIG. 8).

Return movement of the handle part 6 is also readily possible in this position of the disc 19, i.e., if necessary, it is possible to open and close the handle part several times, if, for example, the operator should wish to position a clip which has already been applied more firmly.

When the handle part 6 is swivelled back, the initial position, illustrated in FIG. 5, is reached again, and so by swivelling the swivel lever 13, a clip can be pushed forwards out of the magazine again. During this advancing movement, the handle part 6 is again locked in the described manner.

What is claimed is:

1. A surgical applicator for U-shaped clips, comprising:
   a handle;
   a tubular shaft adjoining said handle;
   a forceps-type applicator tool at the free end of said tubular shaft;
   a closing mechanism for said applicator tool arranged in said tubular shaft and actuatable from said handle;
   an advancing mechanism for said clips arranged in said tubular shaft and also actuatable from said handle;
   two separate actuating elements on said handle which are each movable between a rest position and a work position, one of said actuating elements being associated with said closing mechanism and the other with said advancing mechanism; and
   a locking member mounted on one of said actuating elements which enters into an operative connection with said other actuating element, thereby preventing each of said two actuating elements from moving so long as the respective other actuating element is not in its rest position; wherein:
   said locking member on said one actuating element is movable between two positions, namely a first release position in which, with said other actuating element in its rest position, said one actuating element is freely movable, and a lock position in which said one actuating element, in any position of said other actuating element, is locked in its movement by said locking member contacting said other actuating element.

2. The surgical applicator of claim 1, wherein:
   said locking member is movable from the release position to the lock position by the movement of said one actuating element from the rest position to the work position and, at the end of this movement, by contact with said other actuating element.

3. The surgical applicator of claim 2, further comprising:
   a spring detent means for releasably fixing said locking member in both the release position and the lock position.

4. The surgical applicator of claim 3, wherein:
   said locking member carries a projection adapted to be pressed in resiliently and having on one side thereof a flat slide flank, and on the other side thereof a steep retaining flank for a part of said other actuating element sliding along said projection;
   said projection only interacts with said sliding part with said locking member in the lock position; and
   said projection is arranged such that said sliding part of said other actuating element contacts said steep retaining flank when said one actuating element is in its rest position.

5. The surgical applicator of claim 3, wherein:
   said locking member is movable from the lock position to the release position by the movement of said other actuating element from the rest position to the work position and, at the end of this movement, by contact with said other actuating element.

6. The surgical applicator of claim 2, further comprising:
   a reversible freewheel mechanism associated with said one actuating element;
   said freewheel mechanism allowing movement of said actuating element in one direction only, and the direction of movement of said freewheel mechanism only being reversible when said actuating element has reached the end points of its path of movement.

7. The surgical applicator of claim 2, wherein:
   said locking member carries a projection adapted to be pressed in resiliently and having on one side thereof a flat slide flank, and on the other side thereof a steep retaining flank for a part of said other actuating element sliding along said projection;
   said projection only interacts with said sliding part with said locking member in the lock position; and
   said projection is arranged such that said sliding part of said other actuating element contacts said steep retaining flank when said one actuating element is in its rest position.

8. The surgical applicator of claim 2, wherein:
   said locking member is movable from the lock position to the release position by the movement of said other actuating element from the rest position to the work position and, at the end of this movement, by contact with said other actuating element.

9. The surgical applicator of claim 1, further comprising:
   a reversible freewheel mechanism associated with said one actuating element;
   said freewheel mechanism allowing movement of said actuating element in one direction only, and the direction of movement of said freewheel mechanism only being reversible when said actuating element has reached the end points of its path of movement.

10. The surgical applicator of claim 9, wherein:
    said locking member is movable from the lock position to the release position by the movement of said other actuating element from the rest position to the work position and, at the end of this movement, by contact with said other actuating element.

11. The surgical applicator of claim 1, wherein:
    said locking member carries a projection adapted to be pressed in resiliently and having on one side thereof a flat slide flank, and on the other side thereof a steep retaining flank for a part of said other actuating element sliding along said projection;
    said projection only interacts with said sliding part with said locking member in the lock position; and
    said projection is arranged such that said sliding part of said other actuating element contacts said steep retaining flank when said one actuating element is in its rest position.

12. The surgical applicator of claim 11, wherein: said locking member is movable from the lock position to the release position by the movement of said other actuating element from the rest position to the work position and, at the end of this movement, by contact with said other actuating element.

13. The surgical applicator of claim 1, wherein:

said locking member is movable from the lock position to the release position by the movement of said other actuating element from the rest position to the work position and, at the end of this movement, by contact with said other actuating element.

14. The surgical applicator of claim 1, wherein:

said one actuating element is associated with said advancing mechanism and said other actuating element with said closing mechanism.

15. The surgical applicator of claim 1, wherein:

said actuating elements are designed as swivel levers on said handle so as to be rotatable about an axis extending transversely to the longitudinal axis of said tubular shaft.

16. A surgical applicator for U-shaped clips, comprising:

a handle;

a tubular shaft adjoining said handle;

a forceps-type applicator tool at the free end of said tubular shaft;

a closing mechanism for said applicator tool arranged in said tubular shaft and actuatable from said handle;

an advancing mechanism for said clips arranged in said tubular shaft and also actuatable from said handle;

two separate actuating elements on said handle which are each movable between a rest position and a work position, one of said actuating elements being associated with said closing mechanism and the other with said advancing mechanism;

a locking member mounted on one of said actuating elements which enters into an operative connection with said other actuating element, thereby preventing each of said two actuating elements from moving so long as the respective other actuating element is not in its rest position; and a reversible freewheel mechanism associated with said one actuating element;

said freewheel mechanism allowing movement of said actuating element in one direction only, and the direction of movement of said freewheel mechanism only being reversible when said actuating element has reached the end points of its path of movement.

17. The surgical applicator of claim 16, wherein:

said locking member carries a projection adapted to be pressed in resiliently and having on one side thereof a flat slide flank, and on the other side thereof a steep retaining flank for a part of said other actuating element sliding along said projection;

said projection only interacts with said sliding part with said locking member in the lock position; and said projection is arranged such that said sliding part of said other actuating element contacts said steep retaining flank when said one actuating element is in its rest position.

18. The surgical applicator of claim 16, wherein:

said locking member is movable from the lock position to the release position by the movement of said other actuating element from the rest position to the work position and, at the end of this movement, by contact with said other actuating element.

19. The surgical applicator of claim 16, wherein:

said one actuating element is associated with said advancing mechanism and said other actuating element with said closing mechanism.

20. The surgical applicator of claim 16, wherein:

said actuating elements are designed as swivel levers on said handle so as to be rotatable about an axis extending transversely to the longitudinal axis of said tubular shaft.

21. A surgical applicator for U-shaped clips, comprising:

a handle;

a tubular shaft adjoining said handle;

a forceps-type applicator tool at the free end of said tubular shaft;

a closing mechanism for said applicator tool arranged in said tubular shaft and actuatable from said handle;

an advancing mechanism for said clips arranged in said tubular shaft and also actuatable from said handle;

two separate actuating elements on said handle which are each movable between a rest position and a work position, one of said actuating elements being associated with said closing mechanism and the other with said advancing mechanism; and a locking member mounted on one of said actuating elements which enters into an operative connection with said other actuating element, thereby preventing each of said two actuating elements from moving so long as the respective other actuating element is not in its rest position, wherein:

said locking member is a disc mounted on said one actuating element for rotation about an axis extending parallel to the axis of rotation of said first actuating element between the release position and the lock position.

22. The surgical applicator of claim 21, wherein:

said disc has two edge recesses lying alongside each other in which a detent member displaceable on said one actuating element in the direction towards the axis of rotation of said disc and resiliently pressed against the edge of said disc engages.

23. The surgical applicator of claim 22, wherein:

said disc is arranged in a recess of said one actuating element, said recess being arranged on the part of said one actuating element located opposite the handle part of said one actuating element and being open at the side towards said other actuating element.

24. The surgical applicator of claim 23, wherein:

said recess is partially closed by a cover plate.

25. The surgical applicator of claim 24, wherein:

said disc has an angular projection adapted to be pressed in resiliently with an edge having two edge sections; and a projection of said other actuating element is arranged beside said edge and runs along one of said edge sections when said one actuating element, with said other actuating element in its rest position, is moved from its rest position to its work position, and along the other of said edge sections when said other actuating element, with said one actuating element in its rest position, is moved from the rest position to the work position.

26. The surgical applicator of claim 22, wherein:

said disc has an angular projection adapted to be pressed in resiliently with an edge having two edge sections; and a projection of said other actuating element is arranged beside said edge and runs along one of said edge sections when said one actuating element, with said other actuating element in its rest position, is moved from its rest position to its work position, and along the other of said edge sections when said other actuating element, with said one actuating element in its rest position, is moved from the rest position to the work position.

27. The surgical applicator of claim 23, wherein:

said disc has an angular projection adapted to be pressed in resiliently with an edge having two edge sections; and a projection of said other actuating element is arranged beside said edge and runs along one of said edge sections when said one actuating element, with said other actuating element in its rest position, is moved from its rest position to its work position, and along the other of said edge sections when said other actuating element, with said one actuating element in its rest position, is moved from the rest position to the work position.

28. The surgical applicator of claim 21, wherein:

said disc has an angular projection adapted to be pressed in resiliently with an edge having two edge sections; and a projection of said other actuating element is arranged beside said edge and runs along one of said edge sections when said one actuating element, with said other actuating element in its rest position, is moved from its rest position to its work position, and along the other of said edge sections when said other actuating element, with said one actuating element in its rest position, is moved from the rest position to the work position.

29. The surgical applicator of claim 28, wherein:

said edge sections are of arcuate shape.

30. The surgical applicator of claim 28, wherein:

said edge sections meet essentially at a right angle; and the path of movement of said projection on said other actuating element, upon swivel movement thereof, is essentially perpendicular to said one edge section and parallel to said other edge section.

31. The surgical applicator of claim 28, wherein:

said projection is mounted on said one actuating element for rotation about the same axis of rotation as said disc and is rotated relative to said disc by a swivel spring into a position protruding over said disc.

32. The surgical applicator of claim 31, wherein:

said swivel spring is a spring rod or a leaf spring.

33. The surgical applicator of claim 31, wherein:

said projection is in the form of a lamina and is received in a central recess of said disc.

34. The surgical applicator of claim 28, wherein:

said disc has stop faces which said projection of said other actuating element contacts; and said projection swivels said disc from the release position to the lock position and vice versa when said one or said other actuating element is in the work position.

35. The surgical applicator of claim 28, wherein:

said projection on said other actuating element is a pin projecting sideways.

36. The surgical applicator of claim 21, wherein:

said one actuating element is associated with said advancing mechanism and said other actuating element is associated with said closing mechanism.

37. The surgical applicator of claim 21, wherein:

said actuating elements are designed as swivel levers on said handle so as to be rotatable about an axis extending transversely to the longitudinal axis of said tubular shaft.

* * * * *